US00H002216H

(19) United States
(12) Statutory Invention Registration
Karcher et al.

(10) Reg. No.: US H2216 H
(43) Published: May 6, 2008

(54) METHOD FOR TESTING FOR BIOACCUMULATION

(75) Inventors: Arron L. Karcher, Duncan, OK (US); J. Michael Wilson, Duncan, OK (US)

(73) Assignee: Halliburton Energy Services, Inc., Duncan, OK (US)

(21) Appl. No.: 10/779,192

(22) Filed: Feb. 14, 2004

(65) Prior Publication Data

US 2005/0182569 A1 Aug. 18, 2005

(51) Int. Cl.

| | |
|---|---|
| ***G06F 19/00*** | (2006.01) |
| ***G01N 33/48*** | (2006.01) |
| ***G01N 33/50*** | (2006.01) |
| ***G01N 31/00*** | (2006.01) |

(52) U.S. Cl. ..... 702/19; 702/23

(58) Field of Classification Search ..... None
See application file for complete search history.

(56) References Cited

PUBLICATIONS

Herbert, Analytical Chemistry, 1995, vol. 67, No. 4, p. 744–749.*

McWilliams et al., Bioaccumulation Potential of Surfactants: A Review, Presented at Chemistry in the Oil Industry VII, Royal Society of Chemistry & EOSCA, Nov. 2001, p. 1–13.*

OECD Guideline for the Testing of Chemicals No. 107, entitled "Partition Coefficient (n–octanol/water): Shake Flask Method," adopted Jul. 27, 1995 by the Council for the Organisation for Economic Co–Operation and Development, Paris, France.

OECD Guideline for the Testing of Chemicals No. 117, entitled "Partition Coefficient (n–octanol/water), High Performance Liquid Chromatography (HPLC) Method," adopted Mar. 30, 1989 by the Council for the Organisation for Economic Co–Operation and Devolopment, Paris, France.

(Continued)

*Primary Examiner*—Michael J. Carone
(74) *Attorney, Agent, or Firm*—Craig W. Roddy; Karen B. Tripp

(57) ABSTRACT

For use in estimating or predicting bioaccumulation of a chemical analyte, even a surfactant, log $P_{ow}$ values for the analyte may be determined by calculating the log of the ratio of the concentrations of the analyte in n-octanol and in water, equilibrated using a slow-stir method. In this method, samples of the analyte are prepared and stirred in n-octanol and water (or other largely immiscible solvents) at a rate sufficiently low to avoid emulsions over time at a constant temperature. After stirring, the n-octanol layer and the water layer are sampled and the quantity of analyte in each measured.

25 Claims, 1 Drawing Sheet

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

METHOD FOR TESTING FOR BIOACCUMULATION

BACKGROUND OF THE INVENTION

1. Field of the Invention

The present invention relates to testing, measuring, analyzing or predicting bioaccumulation and is particularly related to a method for laboratory testing or determining log $P_{ow}$ values of chemical substances for relating to the bioaccumulation of such substances. The method is notably suitable for measuring or evaluating bioaccumulation of surfactants, although the method may also be used for measuring or evaluating bioaccumulation of other chemical substances.

2. Description of Relevant Art

Bioaccumulation is generally defined as the process through which a chemical increases in concentration in a biological organism over time when compared to the concentration of the chemical in the environment. Compounds accumulate in living things any time they are taken up and stored faster than they are broken down, metabolized or excreted. The process is normal and can be helpful to life, as in the storage of vitamins, for example. However, the process can result in injury to life when the equilibrium between exposure and bioaccumulation is overwhelmed. The extent of bioaccumulation depends on the concentration of the chemical in the environment, the amount of chemical coming into an organism from the food, air or water, and the time it takes for the organism to acquire the chemical and then store, metabolize or degrade, and excrete it. The nature of the chemical itself, such as its solubility in water and fat, affects its uptake and storage; the ability of the organism to degrade and excrete the chemical also affects its uptake and storage. Understanding the dynamic process of bioaccumulation is generally viewed as important in protecting humans and other organisms from adverse effects from chemical exposure. Consequently, bioaccumulation has become a critical consideration in the regulation of chemicals.

Industries using chemicals in the environment are increasingly faced with regulations concerning bioaccumulation of those chemicals. The oil and gas industry has varying guidelines and regulations in many countries worldwide relating to chemicals used in the search for and production of hydrocarbons from subterranean formations in those countries. Some regulations require testing of individual components of chemicals used. For compliance with such guidelines and regulations, the industry tests its chemicals and chemical components, often by test methods or techniques also prescribed, recommended, and/or approved in the guidelines or regulations.

One such test is the OECD Guideline for Testing of Chemicals No. 117, concerning the Partition Coefficient (n-octanol/water), High Performance Liquid Chromatography (HPLC) Method, incorporated herein in its entirety by reference and available from the Organisation for Economic Co-operation and Development in Paris, France. This test is performed on analytical columns packed with a commercially available solid phase containing long hydrocarbon chains (e.g., $C_8$–$C_{18}$) chemically bound onto silica. Chemicals injected onto such a column move along it by partitioning between the mobile solvent phase and the hydrocarbon stationary phase. The chemicals are retained in proportion to their hydrocarbon-water partition coefficient, with water-soluble chemicals eluted first and oil-soluble chemicals eluted last. This pattern enables the relationship between the retention time on a reverse-phase column and the n-octanol/water partition coefficient to be established. The partition coefficient is deduced from the capacity factor, k, given by the formula:

$$k = \frac{t_R - t_o}{t_o}$$

where $t_R$ is the retention time of the test substance, and $t_o$ is the dead-time, i.e., the average time an unretained molecule needs to pass through the column. Quantitative analytical methods are not needed and only the retention times are measured.

The partition coefficient (P) is the ratio of the equilibrium concentrations of a dissolved substance in a two-phase system consisting of two largely immiscible solvents. For n-octanol and water, the partition coefficient is the quotient of the concentrations of the two, expressed as follows, but usually written in the form of its logarithm to base ten:

$$P_{ow} = \frac{c_{n\text{-}octanol}}{c_{water}}$$

$P_{ow}$ is a key parameter in studies of the environmental impact of chemical substances. The OECD Guideline No. 117 states that there is a highly-significant relationship between the $P_{ow}$ of substances and their bioaccumulation in fish and that $P_{ow}$ is useful in predicting adsorption on soil and sediments and in establishing quantitative structure-activity relationships for a wide range of biological effects.

The HPLC method or test can be used in determining $P_{ow}$ values in the range log $P_{ow}$ between 0 and 7. A preliminary estimation of $P_{ow}$, generally done through known calculation methods, is needed. When the $P_{ow}$ values are in the range log $P_{ow}$ between −2 and 4, another test has been used. That test is the OECD Guideline for Testing of Chemicals No. 107, called the Partition Coefficient (n-octanol/water): Shake-Flask Method, which is incorporated herein in its entirety by reference and available from the Organisation for Economic Co-operation and Development in Paris, France.

The Shake-Flask Method is based on the principle that the Nernst partition law applies at constant temperature, pressure and pH for dilute solutions. OECD Guideline No. 107 states that the law strictly applies to a pure substance dispersed between two pure solvents and when the concentration of the solute in either phase is not more than 0.01 mole per liter. If several different solutes occur in one or both phases at the same time, the results may be affected. Dissociation or association of the dissolved molecules cause deviations from the partition law.

Neither the HPLC Method nor the Shake-Flask Method may be used for determining log $P_{ow}$ values for measuring or evaluating bioaccumulation for chemicals that are considered surface active, or for surfactants. Nevertheless, surfactants are commonly used in drilling and well treating fluids. A need exists for effective new techniques or methods for determining the $P_{ow}$ values of various surfactants.

SUMMARY OF THE INVENTION

The present invention provides a new method for testing for bioaccumulation of chemicals. The method has the advantage of affording calculation of $P_{ow}$ values for surfactants. Moreover, the method does not require separation of individual components of surfactant mixtures, and advantageously enables a bulk analysis of all of the mixture components.

The present invention uses a slow-stir (or no-stir) method in which the test substance is allowed to equilibrate between two largely immiscible solvents, preferably octanol and water, in a container maintained at a fixed or constant temperature below the boiling point of the solvents and the test substance. Preferably that temperature does not vary more than one ° C. during the test. Stirring reduces the time needed for equilibration and slow stirring is used to eliminate the tendency for emulsions to form during the test. (Such emulsion formation is common with Shake Flask measurements). That is, any speed sufficiently slow to prevent emulsion formation is believed sufficiently slow for the test of the invention. Generally, the speed selected will depend on the size and shape of the container and the length of the stirring bar (if a stirring bar is used), as well as the ease the solvents form emulsions. The period of time for the slow stirring may be several days or a few weeks and preferably should be sufficiently long to allow equilibration.

After stirring, the concentration of the test substance is measured or determined in both phases. A light scattering detector or an ionized mass detector (mass spectroscopy) are preferred when the test substance is a surfactant as these instruments are capable of measuring concentrations of surfactants below the critical micelle concentration (CMC), although other equipment or techniques capable of determining concentration of the test substance might alternatively be used. From these concentration measurements, the partition coefficient and preferably also log P (or log $P_{ow}$ when octanol and water are the solvents) are calculated.

DETAILED DESCRIPTION OF PREFERRED EMBODIMENTS

Figure 1:
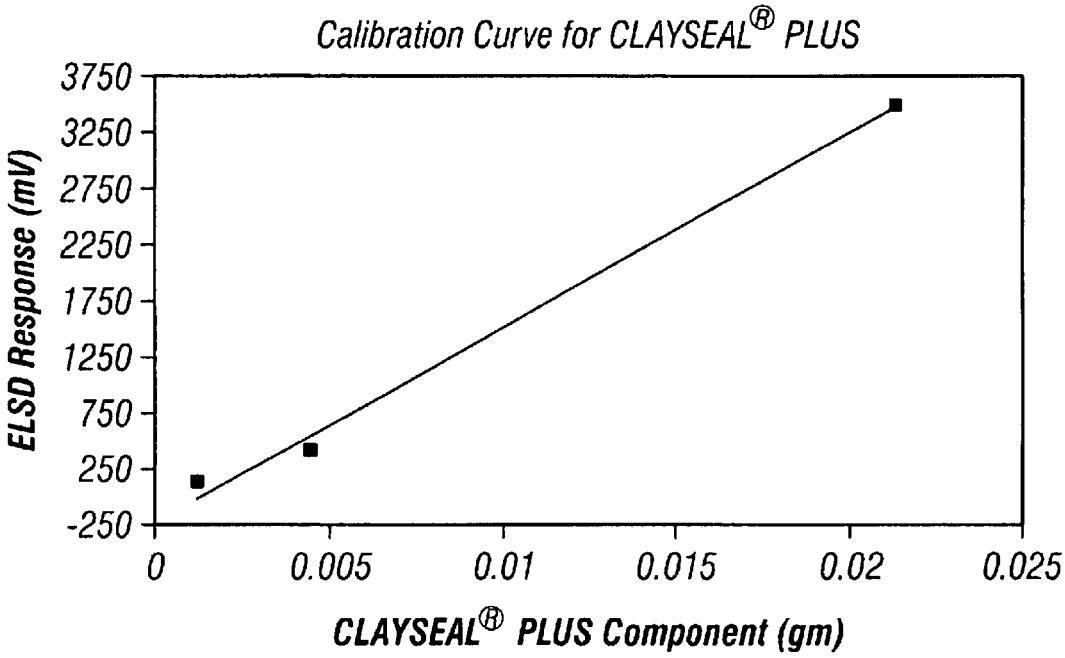
FIG. 1 is a calibration curve for a test surfactant used.

In the method of the present invention, the log $P_{ow}$ for a test substance or chemical analyte is obtained through a slow-stir (or no-stir) procedure, typically conducted in a laboratory or under laboratory type conditions using laboratory type equipment. Initially, two largely, substantially, or entirely immiscible solvents are selected for the analyte. Water and octanol are preferred solvents and preferably the water will be distilled or double-distilled and preferably the octanol will be of analytical grade or higher. Other largely immiscible solvents that may be used include (without limitation) oil and alcohol combinations as well as more common oil and water or other alcohol and water combinations.

After selection, these immiscible solvents are presaturated with—typically about 10% of—each other for at least 24 hours. That is, for example, the water is presaturated with octanol and the octanol is presaturated with water. Following this, these solvents are used to prepare stock solutions with the analyte for testing.

Samples of the stock solutions containing a known concentration of analyte are allowed to equilibrate and the concentration of analyte in each solvent layer is measured for calculation of the partition coefficient (P). Stirring reduces the time needed for equilibration. Preferably the samples are stirred at a constant temperature (preferably not varying by more than 1° C.) and at a slow rate so that emulsions do not begin to form in the samples. The temperature selected may be any temperature that is below the boiling point of the two solvents and the test analyte. For an octanol-water system, a temperature selected from the range of about 20° C. to about 22° C. is preferred, although higher temperatures such as about 25° C. may alternatively be used. Generally, the stirring speed (if any) selected will depend on the size and shape of the container and the length of the stirring bar (if a stirring bar is used), as well as the ease the solvents form emulsions. For surfactants generally, a stir rate that creates a vortex no greater than simply reaching from the top to the bottom of the container may often be preferred, or more preferably a stirring rate that creates a vortex that does not exceed about one-fifth the height of the total fluid column. For example, for the tests discussed in the Experimental section below, test vials having dimensions of 27.5 mm×70 mm were used and about a 15 mm vortex (or less) was preferred. This provided a length of fluid column/vortex height ratio of about 4.667. To achieve such a ratio, a stirring rate of about 150 rpm was used. However, speeds for example ranging from 0 rpm to 200 rpm may reasonably be considered for use for most surfactants tested, in this size vials for purposes of the present invention. A length of fluid column/vortex height ratio in the range of about 1 (for the case where the vortex extends from the top to the bottom of the container) to infinity ∞ (for the case of no stirring) may be used in the present invention so long as emulsions do not form.

After such stirring, typically for several days or weeks, preferably until equilibration is reached, the concentration of the analyte is measured in each immiscible layer, for example, in the water layer ($c_{water}$) and in the octanol layer ($C_{n\text{-}octanol}$) and the $P_{ow}$ value for the analyte is calculated using the following formula:

$$P_{ow} = \frac{c_{n\text{-}octanol}}{c_{water}}$$

If solvents other than water and n-octanol are used, the heavier solvent is substituted for the $c_{water}$ in the ratio and the lighter solvent is substituted for the $C_{n\text{-}octanol}$ in the ratio, as follows:

$$P = \frac{c_{(lighter\ solvent)}}{c_{(heavier\ solvent)}}$$

Samples for this concentration analysis are taken from each solvent layer, for example the water layer and the octanol layer, preferably immediately after stirring but in any case before about 1 hour has lapsed after stirring has ceased or after equilibrium is believed to have been reached. These samples may then be immediately analyzed for content and concentration of analyte or may be stored, preferably at a constant temperature in the range of about 20° C. to about 22° C. or at room temperature, for later analysis. Measurement of the concentration of the analyte may be conducted with any equipment capable or suitable for this purpose. For example, a light scattering detector or an ionized mass detector (mass spectroscopy) is preferred when the analyte is a surfactant as these instruments are capable of measuring concentrations of surfactants below their critical micelle concentration (CMC). When the analyte has no chromaphore for detection, an evaporative light scattering detector is preferred.

Preferably, such sampling and measurements of the analyte concentration in each layer and calculation of the partition coefficient and log $P_{ow}$ value (or log P value if solvents other than octanol and water are used) are made periodically during the test to better ascertain when equilibrium is reached. Equilibrium is considered reached when the log $P_{ow}$ value does not vary more than about 0.3 per measurement, or when the analyte concentration in the layers appears stable. At equilibrium, the $P_{ow}$ value and the log $P_{ow}$ value are final values for the analyte and are available for use in evaluating bioaccumulation of the analyte.

Experiments

In an experiment demonstrating the invention, two surfactants were used as test analytes—surfactant COEO and surfactant LAEO. The analytes were each dried under vacuum to remove excess water, after which a small portion of the resulting dried residue was weighed and mixed in a sufficient amount of n-octanol saturated water to make stock solutions having the concentrations set forth in Table 1. (Stock solutions could alternatively have been prepared in water saturated n-octanol).

TABLE 1

Initial Surfactant Concentrations

| Surfactant ID | Stock Solution Concentration (mg/ml) |
|---|---|
| COEO | 1.095 |
| LAEO | 1.260 |

Following dissolution of the analytes, test samples were prepared as indicated in Table 2.

TABLE 2

Test Conditions for the Surfactants

| Sample ID | Vol. Stock Solution (ml) | Vol. Octanol (ml) | Vol. Water (ml) | Slow-stir Time (hr) |
|---|---|---|---|---|
| COEO-A | 1.0 | 15.0 | 14.0 | 91 |
| COEO-B | 1.0 | 15.0 | 14.0 | 115 |
| COEO-C | 1.0 | 15.0 | 14.0 | 144 |
| LAEO-A | 1.0 | 15.0 | 14.0 | 91 |
| LAEO-B | 1.0 | 15.0 | 14.0 | 115 |
| LAEO-C | 1.0 | 15.0 | 14.0 | 144 |

The test samples were kept at a constant temperature of 22.0° C. (+/−1.0° C.) and stirred for the times indicated in Table 2 at a rate sufficiently slow as to avoid emulsion formation. Immediately after stirring, aliquots from the test samples were taken from the water layer and from the octanol layer for analysis in an evaporative light scattering detector. The data was plotted and the peak area of the octanol layer was divided by the peak area of the water layer for each sample. The logarithm of these ratios are listed as results in Table 3.

TABLE 3

Log $P_{ow}$ Values as Measured by the Slow-Stir Method

| Sample ID | Log $P_{ow}$ |
|---|---|
| COEO-A | −0.32 |
| COEO-B | −0.18 |
| COEO-C | −0.55 |
| LAEO-A | 1.13 |
| LAEO-B | 1.11 |
| LAEO-C | 0.72 |

These log $P_{ow}$ values for the surfactants were consistent and reproducible for all three sampling times, thus assuring sample equilibrium.

In another experiment, CLAYSEAL® PLUS drilling fluid additive, available from Halliburton Energy Services, Inc. in Duncan, Okla. and Houston, Tex., was used as the test analyte. Three samples were prepared by drying and weighing the analyte and then adding a certain quantity of it to 15 ml of n-octanol saturated water to yield a test stock solution containing 0.021 g/ml of the analyte. Next 3 ml of this stock solution was pipetted into a test jar along with 12 ml more of the n-octanol saturated water. Finally, 15 ml of water saturated n-octanol was added to the jar along with a magnetic stir bar. The samples were magnetically slow stirred at a constant temperature of 20.0° C. and a slow rate so that there was a small vortex (less than about 15 mm in test vials 27.5 mm×70 mm to avoid forming any emulsions inside the test samples) for 86 hours. After stirring, the n-octanol and water layers were sampled and the aliquots stored at room temperature until further analysis.

For quantification, the aliquots were analyzed by a flow injection technique using an Agilent 1100 series HPLC capable of injecting small amounts (25 μl) of each sample directly into an evaporating light scattering detector (ELSD) from Polymer Labs. Since the solvents were both volatile at the optimized detection temperature of the detector, there was no need to develop any separation methods. All samples were analyzed as duplicates. Also, the original test stock solution was diluted in series and analyzed in the same manner for data to create a calibration curve to quantify the amount of analyte in both the n-octanol and water phases. Further, both water and n-octanol blanks were analyzed to test for any background noise.

The calibration curve is shown in FIG. 1. From this curve, the average amount of the CLAYSEAL® PLUS drilling fluid additive analyte in the water layer was 61.8 mg. The n-octanol layer yielded no measurable signal. Overall, the total amount of CLAYSEAL® PLUS drilling fluid additive analyte initially placed in the test jars was 63.2 mg. Therefore, within experimental error, the entire amount of the analyte appeared to be totally incorporated into the water phase.

To calculate the log $P_{ow}$ for CLAYSEAL® PLUS drilling fluid additive, it was necessary to incorporate some constraints on the limits of detectability of the analyte in the n-octanol phase, since the amount present was nondetectable. It was concluded that the highest amount possible in the n-octanol phase was 2.1 mg. This number was twice the amount of the smallest standard used to construct the calibration curve. By taking this approach, any error incorporated into the final result was on the side of resulting in a higher rather than lower log $P_{ow}$ value. (Lower log $P_{ow}$ values are considered indicative of lesser environmental impact, so the approach taken was a worse-case scenario approach). Using this number, the log $P_{ow}$ for CLAYSEAL® PLUS drilling fluid additive was calculated to be −1.5.

The foregoing description of the invention is intended to be a description of preferred embodiments. Various changes in the details of the described method can be made without departing from the intended scope of this invention as defined by the appended claims.

What is claimed is:

1. A method for obtaining a log P value of a chemical for use in chemical bioaccumulation analysis, said method comprising:

providing a sample of said chemical in two largely immiscible solvents;

allowing said sample to equilibrate at constant temperature over time;

determining the concentration of the chemical in each of the solvents; and calculating the partition coefficient.

2. The method of claim 1 further comprising stirring said sample to expedite said equilibration at a rate sufficiently slow that emulsions do not occur.

3. The method of claim 1 wherein said chemical is a surfactant.

4. The method of claim 1 wherein said solvents are water and n-octanol.

5. The method of claim 4 wherein said temperature is in the range of about 20° C. to about 22° C.

6. The method of claim 1 wherein said temperature is below the boiling point of said solvents and said chemical.

7. The method of claim 1 wherein said time extends over several days or weeks.

8. The method of claim 4 wherein said calculation is made using the equation:

$$P_{ow} = \frac{c_{n\text{-}octanol}}{c_{water}}.$$

9. A method for obtaining a log P value of a surfactant for use in surfactant bioaccumulation analysis, said method comprising:

providing a sample of said surfactant in two largely immiscible solvents, stirring said sample at constant temperature and at a rate sufficiently slow that emulsions do not occur over time while allowing equilibration of said sample;

determining the concentration of the surfactant in each solvent, and calculating the partition coefficient of the surfactant.

10. The method of claim 9 wherein said rate of stirring provides a vortex in said sample such that the ratio of the length of the fluid column of said sample to the vortex height ranges from about 1 to about ∞.

11. The method of claim 9 wherein said rate of stirring provides a vortex in said sample such that the ratio of the length of the fluid column of said sample to the vortex height ranges from about 4 to 5.

12. The method of claim 9 wherein said partition coefficient is calculated using the following formula:

$$P = \frac{c_{(lighter\ solvent)}}{c_{(heavier\ solvent)}}.$$

13. The method of claim 9 wherein the solvents are water and n-octanol and the following equation is used in calculating said partition coefficient:

$$P_{ow} = \frac{c_{n\text{-}octanol}}{c_{water}}.$$

14. The method of claim 13 wherein said temperature is in the range of about 20° C. to about 22° C.

15. The method of claim 9 wherein said temperature is below the boiling point of said solvents and said surfactants.

16. A method for obtaining the partition coefficient of a surfactant analyte dissolved in a two-phase system consisting of two largely immiscible solvents wherein said analyte is allowed to reach equilibrium in said system while avoiding the formation of emulsions.

17. The method of claim 16 wherein said equilibrium is reached through slow stirring.

18. The method of claim 17 wherein said stirring causes a vortex in said system such that the ratio of the length of the fluid column of said system to the vortex height ranges from about 1 to ∞.

19. The method of claim 17 wherein said stirring causes a vortex in said system such that the ratio of the length of the fluid column of said system to the vortex height ranges from about 4 to 5.

20. The method of claim 16 wherein said partition coefficient is calculated using the formula:

$$P = \frac{c_{lighter\ phase}}{c_{heavier\ phase.}}.$$

21. The method of claim 16 wherein said equilibrium is reached while maintaining the surfactant analyte and solvents at constant temperature.

22. The method of claim 21 wherein said temperature is below the boiling point of said system.

23. The method of claim 21 wherein the two-phase system is n-octanol and water and said partition coefficient is calculated using the formula:

$$P_{ow} = \frac{c_{n\text{-}octanol}}{c_{water.}}.$$

24. The method of claim 23 wherein said temperature is in the range of about 20° C. to about 25° C.

25. The method of claim 16 comprising calculating the logarithm in base 10 of said partition coefficient for use in bioacculation analysis.

* * * * *